(12) United States Patent
Utsugi et al.

(10) Patent No.: US 8,357,471 B2
(45) Date of Patent: *Jan. 22, 2013

(54) SECONDARY BATTERY USING AN ELECTROLYTE SOLUTION

(75) Inventors: Koji Utsugi, Tokyo (JP); Yuki Kusachi, Tokyo (JP); Tsuyoshi Katou, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,783

(22) Filed: Oct. 17, 2011

(65) Prior Publication Data

US 2012/0034517 A1    Feb. 9, 2012

Related U.S. Application Data

(62) Division of application No. 10/541,063, filed as application No. PCT/JP2004/018698 on Dec. 15, 2004.

(30) Foreign Application Priority Data

Dec. 15, 2003 (JP) .................. 2003-416516
Oct. 29, 2004 (JP) .................. 2004-317301

(51) Int. Cl.
*H01M 6/16* (2006.01)
(52) U.S. Cl. ............................. 429/340; 429/339
(58) Field of Classification Search ........... 429/339–340
See application file for complete search history.

(56) References Cited

U.S. PATENT DOCUMENTS

| | | | |
|---|---|---|---|
| 4,818,644 A | 4/1989 | Armand | |
| 4,950,768 A | 8/1990 | Cronyn | |
| 5,795,674 A | 8/1998 | Shiota | |
| 6,225,009 B1 | 5/2001 | Fleischer et al. | |
| 6,436,582 B1 | 8/2002 | Hamamoto et al. | |
| 6,620,546 B1 | 9/2003 | Michot et al. | |
| 7,163,768 B2 | 1/2007 | Utsugi et al. | |
| 7,482,302 B2 | 1/2009 | Adachi et al. | |
| 2002/0037458 A1 | 3/2002 | Yamaguchi et al. | |
| 2003/0113621 A1* | 6/2003 | Shimamura et al. ......... 429/162 |
| 2004/0043300 A1 | 3/2004 | Utsugi et al. | |
| 2004/0214091 A1 | 10/2004 | Lim et al. | |
| 2006/0272950 A1 | 12/2006 | Martyak et al. | |

FOREIGN PATENT DOCUMENTS

| | | |
|---|---|---|
| CA | 2 321 373 | 3/2001 |
| EP | 1 088 814 | 4/2001 |
| EP | 1215304 A1 | 6/2002 |
| JP | 5-44946 | 7/1993 |
| JP | 05-234583 | 9/1993 |
| JP | 05-275077 | 10/1993 |
| JP | 07-263378 | 10/1995 |
| JP | 07-302617 | 11/1995 |
| JP | 08-250108 | 9/1996 |
| JP | 09-245834 | 9/1997 |
| JP | 09301981 | 11/1997 |
| JP | 10-189041 | 7/1998 |
| JP | 11-288706 | 10/1999 |
| JP | 2996234 | 10/1999 |
| JP | 2000-003724 | 1/2000 |
| JP | 3024636 | 1/2000 |
| JP | 2000-133304 | 5/2000 |
| JP | 2000-133305 | 5/2000 |
| JP | 3120789 | 10/2000 |
| JP | 2001-313071 | 11/2001 |
| JP | 2002-008718 | 1/2002 |
| JP | 2002-170564 | 6/2002 |
| JP | 2003-007334 | 1/2003 |
| JP | 2003-115324 | 4/2003 |
| JP | 3417411 | 4/2003 |
| JP | 2003-157900 | 5/2003 |
| JP | 2003-217654 | 7/2003 |
| JP | 2004-193408 | 7/2004 |
| KR | 20010067251 | 7/2001 |
| SU | 379659 | 1/1971 |
| SU | 644858 | 1/1979 |
| WO | 85/03075 | 7/1985 |
| WO | WO 85/03075 | 7/1985 |
| WO | WO 2004072021 A1 | 8/2004 |
| WO | 2004/101860 | 11/2004 |

OTHER PUBLICATIONS

Saltovskaya, L.A. et al.—Extraction of copper from secondary copper-containing ores—SciFinder—SciFinder Citation for SU 644858 A.—Jan. 30, 1979.
U.S Official Action from corresponding U.S. Appl. No. 10/541,063—Nov. 14, 2011, Jun. 17, 2011, Apr. 25, 2011, Feb. 3, 2011, Aug. 11, 2010, Dec. 8, 2009, Jul. 22, 2009 & Dec. 11, 2008.
U.S. Official Action from corresponding U.S. Appl. No. 10/582,855—Sep. 8, 2011, Jan. 7, 2011, Sep. 27, 2010, Apr. 15, 2010 & Sep. 17, 2009.
Derwent Abstract for Frediani, EP 1215304 A1.
CAS citation for Frediani, EP 1215304 A1.
Machine Translation for Julji et al., JP 09-301981 A.
Journal of American Pharmaceutical Association, vol. 126, pp. 485-493, Jun. 1937.
G. Schroeter, Lieb, Ann Der Chemie, vol. 418, pp. 161-257 (1919).
Biol. Aktiv. Soedin., pp. 64-69 (1968).
Armyanskii Khimicheskii Zhurnal, 21, pp. 393-396 (1968).
United States Official Action—U.S. Appl. No. 10/541,063—Aug. 21, 2012.

*Primary Examiner* — Patrick Ryan
*Assistant Examiner* — Muhammad Siddiquee
(74) *Attorney, Agent, or Firm* — Young & Thompson

(57) ABSTRACT

There is provided a lithium secondary battery which has excellent characteristics such as energy density and electromotive force and is excellent in cycle life and storage stability. An electrolyte solution for secondary battery comprising at least an aprotic solvent having an electrolyte dissolved therein and a compound represented by the general formula (1).

6 Claims, 1 Drawing Sheet

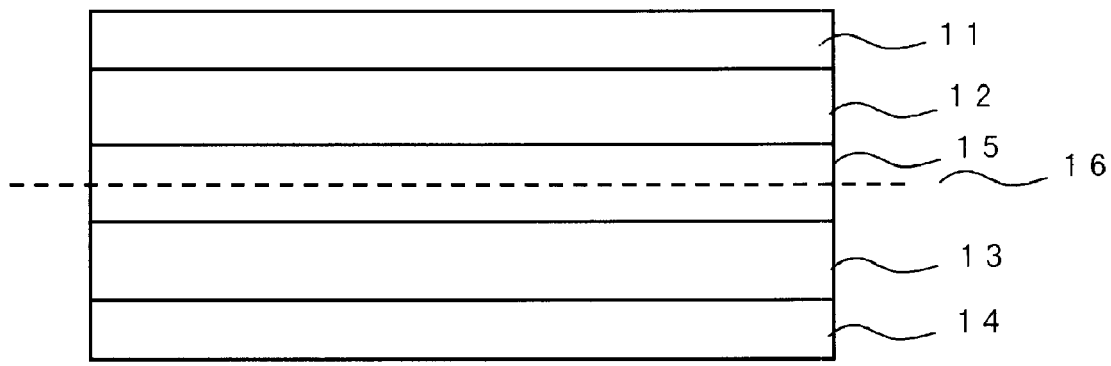

SECONDARY BATTERY USING AN ELECTROLYTE SOLUTION

CROSS REFERENCE TO RELATED APPLICATIONS

This application is a division of co-pending application Ser. No. 10/541,063 filed on Jun. 29, 2005, which is a National Stage of PCT/JP2004/018698 filed on Dec. 15, 2004, which claims foreign priority to Japanese Application Nos. 2003-416516 and 2004-317301 filed on Dec. 15, 2003 and Oct. 29, 2004. The entire content of each of these applications is hereby expressly incorporated by reference.

TECHNICAL FIELD

The present invention relates to an additive used for an electrolyte solution for an electrochemical device, an electrolyte solution for secondary battery and a secondary battery using the same.

BACKGROUND ART

A non-aqueous electrolyte solution type lithium-ion or lithium secondary battery in which a carbon material or lithium metal is used in an anode while a lithium-containing complex oxide is used in a cathode has drawn attention as an electric source for a cellular phone, a notebook computer or the like because it can realize a higher energy density. It is generally known that in such a secondary battery, a film which is called a surface film, a protective film, an SEI or a membrane is formed on an electrode surface. It is also well-known that controlling the surface film is essential for improving electrode performance because the surface film significantly influences a charge/discharge efficiency, a cycle life and safety. Specifically, when using a carbon material as an anode material, its irreversible capacity must be reduced, and in a lithium-metal anode, a charge/discharge efficiency must be reduced while a safety problem due to dendrite formation must be solved.

There have been suggested a variety of procedures for solving the problems. For example, there has been suggested that a membrane layer made of, e.g., lithium fluoride is formed on a surface of lithium metal by a chemical reaction when using lithium metal as the anode material, to minimize formation of dendrites.

Japanese Patent Application No. 1995-302617 has disclosed that a lithium anode is exposed to an electrolyte solution containing hydrofluoric acid for initiating a reaction of the anode with hydrofluoric acid to coat the surface with a lithium fluoride film. Hydrofluoric acid is generated by a reaction of $LiPF_6$ with a small amount of water. On the other hand, a surface film of lithium hydroxide or lithium oxide is formed on the surface of the lithium anode by autoxidation in the air. These react to form a surface film of lithium fluoride on the anode surface. However, since the lithium fluoride film is formed by utilizing a reaction of an electrode interface with a liquid, the surface film may tend to be contaminated with byproducts, leading to an uneven film. Sometimes, a surface film of lithium hydroxide or lithium oxide may not be formed as an even film or in some area lithium metal may be exposed. Such cases may lead to not only an uneven film, but also a safety problem due to a reaction of lithium with water or hydrofluoric acid. An insufficient reaction may lead to a residue of undesired compounds other than fluoride, which may be harmful by causing reduction in anion conductivity. Furthermore, in a process for forming a fluoride layer utilizing a chemical reaction in such an interface, there are limitations to fluorides or electrolyte solutions which can be used. It is, therefore, difficult to form a stable surface film in a good yield.

In Japanese Patent Application No. 1996-250108, a mixed gas of argon and hydrogen fluoride is reacted with an aluminum-lithium alloy to form a surface film of lithium fluoride on an anode surface. However, if a preformed surface film is present on the surface of lithium metal, in particular if a plurality of components are present, the reaction tends to be uneven, which may make it difficult to form an even lithium fluoride film. In such a case, a lithium secondary battery exhibiting satisfactory cycle properties cannot be obtained.

Japanese Patent Application No. 1999-288706 has disclosed that a surface membrane structure comprising a substance with a rock-salt type crystal structure as a main component is formed on a lithium sheet in which an even crystal structure, i.e., a (100) crystal face, is preferentially oriented. It has been thus described that an even precipitation/dissolution reaction, i.e., an even battery charge/discharge can be achieved, resulting in prevention of dendrite precipitation of lithium and improvement in a battery cycle life. A substance used in a surface film preferably comprises a lithium halide, which is preferably comprised of at least one selected from the group consisting of LiCl, LiBr and LiI and its solid solution with LiF. Specifically, for forming a solid solution membrane of at least one selected from the group consisting of LiCl, LiBr and LiI with LiF, a lithium sheet formed by pressing (rolling) in which a (100) crystal face is preferentially oriented is immersed in an electrolyte solution containing at least one selected from group consisting of (1) chlorine molecules or chloride ions, (2) bromine molecules or bromide ions, and (3) iodine molecules or iodide ions and containing fluorine molecules or fluoride ions to form an anode for a non-aqueous electrolyte battery. In this technique, an rolled lithium metal sheet is used. Since the lithium sheet tends to be exposed in the air, a membrane derived from moisture and so on may be formed on its surface, leading to uneven distribution of active sites. It may be, therefore, difficult to form a desired stable surface film. Thus, this technique has not always been effective for adequately preventing dendrite formation.

There has been described a technique that a capacity and a charge/discharge efficiency can be improved when using as an anode a carbon material such as graphite and hard carbon in which lithium ions can be occluded and released.

Japanese Patent Application No. 1993-234583 has suggested an anode where a carbon material is coated with aluminum, whereby reductive decomposition of a solvent molecule in a solvate with a lithium ion on the carbon surface is reduced to minimize reduction in a cycle life. However, since aluminum reacts with a small of moisture, repeated cycles may lead to rapid reduction in a capacity.

Japanese Patent Application No. 1993-275077 has suggested an anode in which a carbon material surface is coated with a film of a lithium-ion conductive solid electrolyte, whereby decomposition of a solvent when using a carbon material can be minimized, so that a lithium ion secondary battery which particularly allows propylene carbonate to be used can be provided. However, change of stress during insertion and removal of lithium ions generates cracks in the solid electrolyte, which may lead to deteriorated properties. Due to unevenness such as crystal defects in the solid electrolyte, an even reaction cannot be achieved in the anode surface, sometimes leading to a reduced cycle life.

Japanese Patent Application No. 2000-3724 has disclosed a secondary battery wherein an anode is made of a graphite-containing material and an electrolyte solution comprises a cyclic and linear carbonate as a main component and 0.1 weight % to 4 weight % both inclusive of 1,3-propanesultone and/or 1,4-butanesultone as a cyclic monosulfonate in the electrolyte solution. It is believed that 1,3-propanesultone or 1,4-butanesultone contributes to formation of a passive membrane on a carbon material surface, which can coat an active and highly crystallized carbon material such as natural or artificial graphite with the passive membrane to prevent decomposition of an electrolyte solution without deterioration of a normal reaction in a battery. Japanese Patent Application No. 2000-133304 and U.S. Pat. No. 6,436,582B1 have described that in addition to a cyclic monosulfonate, a linear disulfonate may be similarly effective. However, using the cyclic monosulfonate in Japanese Patent Application No. 2000-3724 or the linear disulfonate in Japanese Patent Application No. 2000-133304 and U.S. Pat. No. 6,436,582B1, a membrane may be formed mainly on an anode while forming a membrane on, for example, a cathode may be substantially difficult. In addition, Japanese Patent Application No. 1993-44946 and U.S. Pat. No. 4,950,768B1 has disclosed a process for preparing a cyclic sulfonate having two sulfonyl groups. J. Am. Pham. Assoc., Vol. 126, pp. 485-493 (1937) and G. Schroeter, Lieb, Ann, Der Chemie, Vol. 418, pp. 161-257 (1919) and Biol. Aktiv. Soedin., pp. 64-69 (1968), Armyanskii Khimicheskii Zhurnal, 21, pp. 393-396 (1968) has disclosed a process for preparing a linear sulfonate.

In Japanese Patent Application No. 2003-7334, an aromatic compound is added to a solvent for an electrolyte solution for preventing oxidation of the solvent for an electrolyte solution to minimize deterioration in a capacity after long-term repetition of charge/discharge of a secondary battery. It is a technique for preventing solvent decomposition by preferentially decomposing the aromatic compound by oxidation. However, when using the additive, sometimes a cathode surface is not coated, resulting in insufficient improvement in cycle properties.

Japanese Patent Application No. 2003-115324 has described that a nitrogen-containing unsaturated cyclic compound is added to an electrolyte solution to improve cycle properties when using a high-voltage cathode. However, while the nitrogen-containing unsaturated cyclic compound can improve a charge/discharge efficiency in an anode, it cannot improve a charge/discharge efficiency in a cathode.

DISCLOSURE OF THE INVENTION

The related art have the following problems in common. Although the surface film generated on the surface of the electrodes has deep influence on charge/discharge efficiency, cycle life and safety depending on their properties, the related art forms a stabilized film mainly on the anode, and no techniques to stably form films on both of the anode and the cathode have been disclosed.

In addition, as for the conventionally used techniques to form a film on the cathode, there has been no technique to enable control of the film over a long period of time. For this reason, although an effect of suppressing dendrite could be obtained to a certain extent at the initial use, when it was used repeatedly, the surface film might be impaired to deteriorate the function as a protection film. This is considered to be attributable to the fact that the occlusion and release of lithium cause changes in volume of the layer of cathode active material containing the lithium while the film formed on the surface thereof scarcely changes in volume and therefore, internal stress occurs within these layers and the interface therebetween. When such internal stress occurs, the surface film is partly damaged, which is supposed to cause deterioration of dendrite suppressing function. This leads to decomposition of the electrolyte solution and consequently it has been difficult to maintain high discharge capacity and excellent cycle characteristic.

Furthermore, even if the conventional technique was used, when carbon materials such as graphite were used for anode, there were cases where electric charge resulted from decomposition of the solvent molecules or anions appeared as an irreversible capacity component, and caused decrease in the initial charge/discharge efficiency. The composition, crystal state, stability, etc. of the film resulted at this stage may significantly adversely affect the subsequent efficiency and the cycle life.

As mentioned above, researches have been conducted aiming at improving charge/discharge efficiency, cycle life and so on by forming a film on the electrode for a secondary battery but films cannot be stably formed on the electrodes (both cathode and anode) and generally, sufficient battery characteristics have not been achieved yet.

The present invention has been made in view of the problems, and the invention forms stabilized films on the surface of electrodes (both cathode and anode) by adding a linear disulfonate in the electrolyte solution for secondary battery and prevents decomposition of the components of the electrolyte solution. Consequently, the invention also aims at providing a secondary battery excellent in cycle characteristic or charge/discharge efficiency.

In order to solve the problems, the present invention has the following construction. That is, the present invention relates to an electrolyte solution for secondary battery comprising at least an aprotic solvent having an electrolyte dissolved therein and a compound represented by the following general formula (1):

[formula 1]

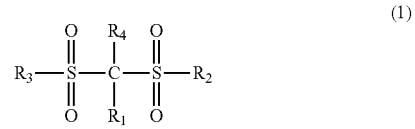

wherein $R_1$ and $R_4$ independently represent an atom or a group selected from a hydrogen atom, a substituted or unsubstituted alkyl group having 1 to 5 carbon atoms, a substituted or unsubstituted alkoxy group having 1 to 5 carbon atoms, a substituted or unsubstituted fluoroalkyl group having 1 to 5 carbon atoms, a polyfluoroalkyl group having 1 to 5 carbon atoms, —$SO_2X_1$, wherein $X_1$ is a substituted or unsubstituted alkyl group having 1 to 5 carbon atoms, —$SY_1$, wherein $Y_1$ is a substituted or unsubstituted alkyl group having 1 to 5 carbon atoms, —COZ, wherein Z is a hydrogen atom or a substituted or unsubstituted alkyl group having 1 to 5 carbon atoms, and a halogen atom; and $R_2$ and $R_3$ independently represent an atom or a group selected from a substituted or unsubstituted alkyl group having 1 to 5 carbon atoms, a substituted or unsubstituted alkoxy group having 1 to 5 carbon atoms, a substituted or unsubstituted phenoxy group, a substituted or unsubstituted fluoroalkyl group having 1 to 5 carbon atoms, a polyfluoroalkyl group having 1 to 5 carbon atoms, a substituted or unsubstituted fluoroalkoxy group having 1 to 5 carbon atoms, a polyfluoroalkoxy group having 1 to 5 carbon atoms, a hydroxyl group, a halogen atom, —$NX_2X_3$, wherein $X_2$ and $X_3$ independently represent a hydrogen atom or a substituted or unsubstituted alkyl group having 1 to 5 carbon atoms, and —NY$_2$CONY$_3$Y$_4$, wherein Y$_2$ to Y$_4$ independently represent a hydrogen atom or a substituted or unsubstituted alkyl group having 1 to 5 carbon atoms.

Furthermore, it is preferable in the present invention that the compound represented by the general formula (1) is contained in the electrolyte solution for secondary battery in an amount of 0.1 to 5.0 weight % based on the total weight of the electrolyte solution for secondary battery.

Furthermore, it is preferable in the present invention that the electrolyte solution for secondary battery further comprises a cyclic monosulfonate represented by the following general formula (2):

[formula 2]

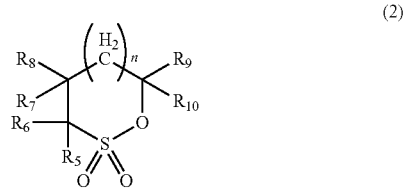

(2)

wherein n is an integer of 0 to 2; R$_5$ to R$_{10}$ independently represent an atom or a group selected from a hydrogen atom, a substituted or unsubstituted alkyl group having 1 to 12 carbon atoms, a substituted or unsubstituted fluoroalkyl group having 1 to 6 carbon atoms, and a polyfluoroalkyl group having 1 to 6 carbon atoms.

Furthermore, it is preferable in the present invention that the electrolyte solution for secondary battery further comprises a cyclic sulfonate having two sulfonyl groups represented by the following general formula (3):

[formula 3]

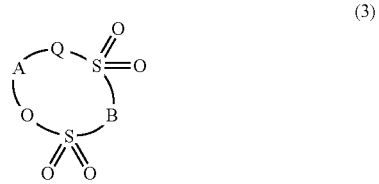

(3)

wherein Q represents an oxygen atom, an methylene group or a single bond, A represents a group selected from a substituted or unsubstituted alkylene group having 1 to 5 carbon atoms, a carbonyl group, a sulfinyl group, a polyfluoroalkylene group having 1 to 5 carbon atoms, a substituted or unsubstituted fluoroalkylene group having 1 to 5 carbon atoms, a substituted or unsubstituted alkylene group having 1 to 5 carbon atoms in which at least one of C—C bonds is converted into a C—O—C bond, a polyfluoroalkylene group having 1 to 5 carbon atoms in which at least one of C—C bonds is converted into a C—O—C bond, and a substituted or unsubstituted fluoroalkylene group having 1 to carbon atoms in which at least one of C—C bonds is converted into a C—O—C bond; and B represents a group selected from a substituted or unsubstituted alkylene group having 1 to 5 carbon atoms, a polyfluoroalkylene group having 1 to 5 carbon atoms, and a substituted or unsubstituted fluoroalkylene group having 1 to 5 carbon atoms.

Furthermore, it is preferable in the present invention that the electrolyte solution for secondary battery further comprises at least one of vinylene carbonate and derivative thereof.

Furthermore, it is preferable in the present invention that the electrolyte solution for secondary battery comprises a lithium salt, and it is preferable that the lithium salt is at least one lithium salt selected from the group consisting of LiPF$_6$, LiBF$_4$, LiAsF$_6$, LiSbF$_6$, LiClO$_4$, LiAlCl$_4$, and LiN(C$_k$F$_{2k+1}$SO$_2$)(C$_m$F$_{2m+1}$SO$_2$), wherein k and m are independently 1 or 2.

Furthermore, it is preferable in the present invention that the aprotic solvent is at least one organic solvent selected from the group consisting of cyclic carbonates, linear carbonates, aliphatic-carboxylates, γ-lactones, cyclic ethers, linear ethers and fluoride derivatives thereof.

Furthermore, it is preferable in the present invention that a secondary battery has a cathode, an anode and an electrolyte solution for secondary battery in which the electrolyte solution for secondary battery is preferably the electrolyte solution for secondary battery.

Furthermore, it is preferable in the present invention that the anode comprises lithium metal or carbon as an anode active material.

Furthermore, it is preferable in the present invention that the anode comprises graphite or amorphous carbon as the carbon.

Furthermore, the present invention is preferably characterized in that the secondary battery is covered with a laminate jacket.

In addition, the present invention relates to an additive for electrolyte solution for an electrochemical device which comprises a compound represented by the following general formula (1).

[formula 4]

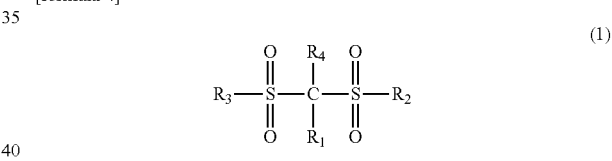

(1)

wherein R$_1$ and R$_4$ independently represent an atom or a group selected from a hydrogen atom, a substituted or unsubstituted alkyl group having 1 to 5 carbon atoms, a substituted or unsubstituted alkoxy group having 1 to 5 carbon atoms, a substituted or unsubstituted fluoroalkyl group having 1 to 5 carbon atoms, a polyfluoroalkyl group having 1 to 5 carbon atoms, —SO$_2$X$_1$, wherein X$_1$ is a substituted or unsubstituted alkyl group having 1 to 5 carbon atoms, —SY$_1$, wherein Y$_1$ is a substituted or unsubstituted alkyl group having 1 to 5 carbon atoms, —COZ, wherein Z is a hydrogen atom or a substituted or unsubstituted alkyl group having 1 to 5 carbon atoms, and a halogen atom; and R$_2$ and R$_3$ independently represent an atom or a group selected from a substituted or unsubstituted alkyl group having 1 to 5 carbon atoms, a substituted or unsubstituted alkoxy group having 1 to 5 carbon atoms, a substituted or unsubstituted phenoxy group, a substituted or unsubstituted fluoroalkyl group having 1 to 5 carbon atoms, a polyfluoroalkyl group having 1 to 5 carbon atoms, a substituted or unsubstituted fluoroalkoxy group having 1 to 5 carbon atoms, a polyfluoroalkoxy group having 1 to 5 carbon atoms, a hydroxyl group, a halogen atom, —NX$_2$X$_3$, wherein X$_2$ and X$_3$ independently represent a hydrogen atom or a substituted or unsubstituted alkyl group having 1 to 5 carbon atoms, and —NY$_2$CONY$_3$Y$_4$, wherein Y$_2$ to Y$_4$ independently represent a hydrogen atom or a substituted or unsubstituted alkyl group having 1 to 5 carbon atoms.

In this specification the terms "polyfluoroalkylene group", "polyfluoroalkyl group" and "polyfluoroalkoxy group" represent corresponding alkylene group, alkyl group and alkoxy group, respectively, in which all the hydrogen atoms bonded to carbon atom are substituted with fluorine atoms, and the terms "fluoroalkylene group", "fluoroalkyl group" and "fluoroalkoxy group" represent corresponding alkylene group, alkyl group and alkoxy group, respectively, in which a part of the hydrogen atoms bonded to carbon atom are substituted with fluorine atom(s).

Furthermore, the term "substituted" in "substituted fluoroalkylene group", "substituted fluoroalkyl group" and "substituted fluoroalkoxy group" represents that at least one of the hydrogen atoms bonded to carbon atom is substituted with an atom or a functional group other than fluorine. The atom or functional group other than fluorine can be, for example, a halogen atom such as a chlorine atom, a bromine atom and an iodine atom, a hydroxyl group, or an alkoxy group having 1 to 5 carbon atoms or a group substituted with a group such as a halogen atom or a hydroxyl group, or a group into which $-SO_2-$ is introduced (for example, $-OSO_2CH_2SO_2Cl$). When a carbon atom is contained in this functional group, this carbon atom shall not be contained in the number of "1 to 5 carbon atoms" in the description of "a substituted or unsubstituted alkyl group having 1 to 5 carbon atoms" and the like.

According to the present invention, an electrolyte solution for secondary battery which contains a linear disulfonate of the present invention in an aprotic solvent is used, and the thus obtained secondary battery is excellent in charge/discharge efficiency, good in cycle characteristics and provides an excellent lithium secondary battery which has a high capacity retention ratio and enables suppression of increase in resistance during storage.

BRIEF DESCRIPTION OF THE DRAWINGS

FIG. 1 is a schematic view illustrating the structure of the secondary battery of the present invention.

DESCRIPTION OF SYMBOLS

Explanations of Letters of Numerals

| | |
|---|---|
| 11 | Cathode current collector |
| 12 | Layer comprising cathode active material |
| 13 | Layer comprising anode active material |
| 14 | Anode current collector |
| 15 | Non-aqueous electrolyte solution |
| 16 | Porous separator |

BEST MODE FOR CARRYING OUT THE INVENTION (Description of the Battery Construction by the Present Invention)

FIG. 1 shows an outlined structure of a battery according to the present invention, which is composed of a cathode current collector 11, a layer 12 comprising the cathode active material which can occlude and release lithium ions, a layer 13 comprising the anode active material which occludes and releases lithium ions, an anode current collector 14, an electrolyte solution 15 and a separator 16. Here, the linear disulfonic acid compound (linear disulfonate) represented by the general formula (1) is contained in the electrolyte solution 15.

(Current Collector)

As the cathode current collector 11, aluminum, stainless steel, nickel, titanium or an alloy thereof can be used, and as the anode current collector 14, copper, stainless steel, nickel, titanium an alloy thereof can be used.

(Separator)

As the separator 16, a porous film such as polyolefin such as polypropylene and polyethylene, and a fluororesin can be preferably used.

(Cathode)

Lithium containing composite oxides usually used can be used as the cathode active material, and specifically materials such as $LiMO_2$, wherein M is selected from Mn, Fe and Co which may be partially substituted with a cation such as Mg, Al, Ti, etc., and $LiMn_2O_4$. The layer 12 which serves as a cathode can be obtained by a method of using a selected cathode active material, distributing and mixing it with a conductive material such as carbon black and a binder such as polyvinylidene fluoride (PVDF) in a solvent such as N-methyl-2-pyrrolidone (NMP), and applying this on the substrate such as an aluminum foil.

(Anode)

The anode active material is composed of lithium metal or a material which can occlude and release lithium such as a carbon material. As a carbon material, graphite, amorphous carbon, diamond-like carbon, fullerene, carbon nanotube, carbon nanohorn, etc. or a composite material thereof which can occlude lithium can be used. When lithium metal is used as an anode active material, the layer 13 which serves as anode can be obtained by an appropriate method such as a melt cooling method, a liquid rapid cooling method, an atomization method, a vacuum vapor deposition method, a sputtering method, a plasma CVD method, a photo CVD method (photo chemical vapor deposition), a thermal CVD and a sol-gel method. When a carbon material is used, the layer 13 which serves as anode can be obtained by mixing the carbon and a binder such as polyvinylidene fluoride (PVDF), then distributing and mixing in a solvent such as NMP followed by applying the mixture on a substrate such as a copper foil method, or a vapor deposition method, a CVD method, a sputtering method.

(Electrolyte Solution)

The electrolyte solution 15 comprises an electrolyte, an aprotic solvent and an additive at least.

(Electrolyte)

In the case of a lithium secondary battery, a lithium salt is used as the electrolyte and dissolved in an aprotic solvent. The lithium salt includes lithium imide salts, $LiPF_6$, $LiAsF_6$, $LiAlCl_4$, $LiClO_4$, $LiBF_4$, $LiSbF_6$, etc. Among these, $LiPF_6$ and $LiBF_4$ are preferable. The lithium imide salt includes $LiN(C_kF_{2k+1}SO_2)(C_mF_{2m+1}SO_2)$, wherein k and m are 1 or 2 independently. These can be used alone or in combination of two or more. High energy density can be attained when such a lithium salt is contained.

(Aprotic Solvent)

As an aprotic electrolyte solution, at least one of organic solvents selected from cyclic carbonates, linear carbonates, aliphatic-carboxylates, γ-lactone, cyclic ether, linear ether, and fluoride derivatives thereof is used. More specifically, one or two or more thereof as a mixture of the following solvents can be used:

Cyclic carbonates: propylene carbonate (hereinafter abbreviated as PC), ethylene carbonate (hereinafter abbreviated as EC), butylene carbonate (BC) and the derivatives thereof;

Linear carbonates: dimethyl carbonate (DMC), diethyl carbonate (hereinafter abbreviated as DEC), ethyl methyl carbonate (EMC), dipropyl carbonate (DPC) and the derivatives thereof;

Aliphatic-carboxylates: methyl formate, methyl acetate, ethyl propionate and the derivatives thereof;

γ-lactones: γ-butyrolactone and the derivatives thereof;

Cyclic ethers: tetrahydrofuran, 2-methyltetrahydrofuran and the derivatives thereof;

Linear ethers: 1,2-diethoxyethane (DEE), ethoxymethoxyethane (EME), diethyl ether, and the derivatives thereof;

Others: dimethylsulfoxide, 1,3-dioxolan, formamide, acetamide, dimethylformamide, acetonitrile, propionitrile, nitromethane, ethylmonoglyme, phosphotriester, trimethoxymethane, dioxolan derivatives, methylsulfolane, 1,3-dimethyl-2-imidazolidinone, 3-methyl-2-oxazolidinone, anisole, N-methylpyrrolidone, fluoride carboxylate.

(Additives)

As an additive, the linear disulfonate represented by the general formula (1) is used.

[formula 5]

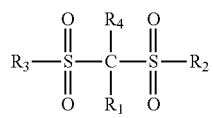

(1)

wherein $R_1$ and $R_4$ independently represent an atom or a group selected from a hydrogen atom, a substituted or unsubstituted alkyl group having 1 to 5 carbon atoms, a substituted or unsubstituted alkoxy group having 1 to 5 carbon atoms, a substituted or unsubstituted fluoroalkyl group having 1 to 5 carbon atoms, a polyfluoroalkyl group having 1 to 5 carbon atoms, $-SO_2X_1$, wherein $X_1$ is a substituted or unsubstituted alkyl group having 1 to 5 carbon atoms, $-SY_1$, wherein $Y_1$ is a substituted or unsubstituted alkyl group having 1 to 5 carbon atoms, $-COZ$, wherein Z is a hydrogen atom or a substituted or unsubstituted alkyl group having 1 to 5 carbon atoms, and a halogen atom; and $R_2$ and $R_3$ independently represent an atom or a group selected from a substituted or unsubstituted alkyl group having 1 to 5 carbon atoms, a substituted or unsubstituted alkoxy group having 1 to 5 carbon atoms, a substituted or unsubstituted phenoxy group, a substituted or unsubstituted fluoroalkyl group having 1 to 5 carbon atoms, a polyfluoroalkyl group having 1 to 5 carbon atoms, a substituted or unsubstituted fluoroalkoxy group having 1 to 5 carbon atoms, a polyfluoroalkoxy group having 1 to 5 carbon atoms, a hydroxyl group, a halogen atom, $-NX_2X_3$, wherein $X_2$ and $X_3$ independently represent a hydrogen atom or a substituted or unsubstituted alkyl group having 1 to 5 carbon atoms, and $-NY_2CONY_3Y_4$, wherein $Y_2$ to $Y_4$ independently represent a hydrogen atom or a substituted or unsubstituted alkyl group having 1 to 5 carbon atoms.

The compound represented by the general formula (1) is an acyclic compound and can be synthesized without cyclization reaction at the time of synthesis, for example by following J. Am. Pham. Assoc., vol. 126, pp. 485-493 (1937); G. Schroeter, Lieb, Ann, Der Chemie, vol. 418, pp. 161-257 (1919); Biol. Aktiv. Soedin., pp 64-69 (1968); Armyanskii Khimicheskii Zhurnal, 21, pp. 393-396 (1968). In addition, the compound can also be obtained as a by-product of the synthesis of cyclic sulfonates having two sulfonyl groups disclosed in Japanese Patent Publication Japanese Patent Application No. 1993-44946. The compound represented by the general formula (1) can be synthesized by easy processes, it has an advantage that an inexpensive electrolyte solution can be provided.

As for the preferable molecule structure, each of $R_1$ and $R_4$ of the general formula (1) is independently an atom or a group selected from a hydrogen atom, an alkyl group having 1 to 5 carbon atoms, a halogen atom and $-SO_2X_1$, wherein $X_1$ is a substituted or unsubstituted alkyl group having 1 to 5 carbon atoms, more preferably independently a hydrogen atom, an unsubstituted alkyl group having 1 to 5 carbon atoms, and still more preferably independently a hydrogen atom or a methyl group from the viewpoint including readiness of formation of a reactive film which occurs on the electrodes, stability of the compound, easiness of handling, solubility in a solvent, easiness of synthesis of the compound and cost. The particularly preferable form of $R_1$ and $R_4$ is the case where $R_1$ and $R_4$ are hydrogen atoms. If $R_1$ and $R_4$ are hydrogen atoms, the methylene moiety between the two sulfonyl groups is activated and it becomes easy to form the reaction film on the electrodes.

As for $R_2$ and $R_3$, each of $R_2$ and $R_3$ is independently an atom or a group selected from a substituted or unsubstituted alkyl group having 1 to 5 carbon atoms, a substituted or unsubstituted alkoxy group having 1 to 5 carbon atoms, a substituted or unsubstituted phenoxy group, a hydroxyl group, a halogen atom, and $-NX_2X_3$, wherein $X_2$ and $X_3$ independently represent a hydrogen atom, a substituted or unsubstituted alkyl group having 1 to 5 carbon atoms, more preferably independently a substituted or unsubstituted alkyl group having 1 to 5 carbon atoms, a substituted or unsubstituted alkoxy group having 1 to 5 carbon atoms, and still more preferably independently either one or both of $R_2$ and $R_3$ are substituted or unsubstituted alkoxy groups having 1 to 5 carbon atoms from the viewpoint including stability of the compound, easiness of synthesis of the compound, solubility in a solvent and cost. For the same reason, the substituted or unsubstituted alkyl group having 1 to 5 carbon atoms is preferably a methyl group or an ethyl group, and the substituted or unsubstituted alkoxy group having 1 to 5 carbon atoms is a methoxy group or an ethoxy group.

The compound of the general formula (1) has two sulfonyl groups, which means that the LUMO thereof is low, and since the compound has LUMO with a value lower than that of the solvent molecule in electrolyte solution, monosulfonate, it is readily reduced. For example, according to semiempirical molecular orbital calculation, LUMO of Compound No. 1 shown in the following table 1 is as low as −0.86 eV. Therefore, the reduced film of Compound No. 1 is presumably formed on the anode prior to the solvent (LUMO: about 1.2 eV) which comprises a cyclic carbonate or linear carbonate, and the reduced film functions to suppress the decomposition of the solvent molecule. Since the decomposition of the solvent molecule is suppressed and the decomposition film of the solvent molecule having a high resistance is hard to be formed on the anode, suppression of increase in resistance and improvement in the cycle characteristics can be expected. It is also supposed that the structure in which two electron-withdrawing sulfonyl groups bind to a carbon atom may activate the carbon atom and promote the film formation on the electrode. Furthermore, it supposed that a carbanion generated by deprotonation of the activated methylene may coordinate to Li or react to form a film on the cathode. Specific examples of the general formula (1) are shown below, but the present invention is not particularly limited to these.

[formula 6]
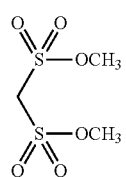
Compound No. 1
[formula 7]
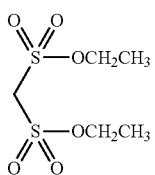
Compound No. 2
[formula 8]
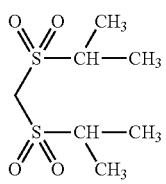
Compound No. 3
[formula 9]
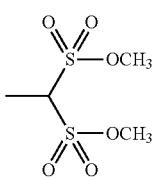
Compound No. 4
[formula 10]
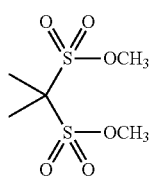
Compound No. 5
[formula 11]
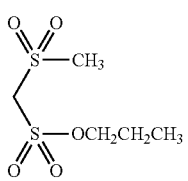
Compound No. 6
[formula 12]
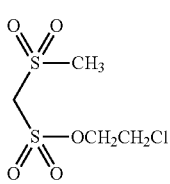
Compound No. 7
[formula 13]
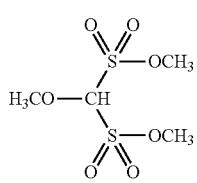
Compound No. 8
[formula 14]
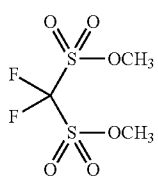
Compound No. 9
[formula 15]
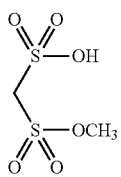
Compound No. 10
[formula 16]
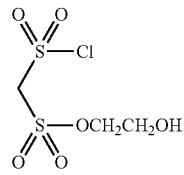
Compound No. 11
[formula 17]
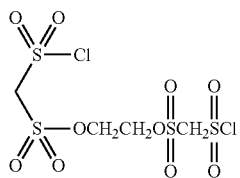
Compound No. 12
[formula 18]
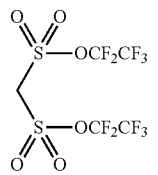
Compound No. 13
[formula 19]
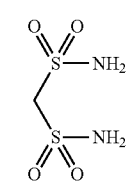
Compound No. 14

[formula 20]

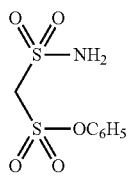

[formula 21]

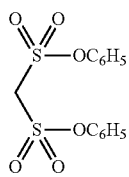

[formula 22]

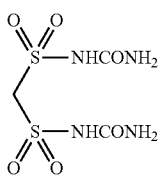

[formula 23]

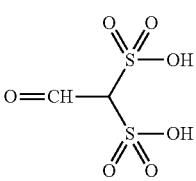

[formula 24]

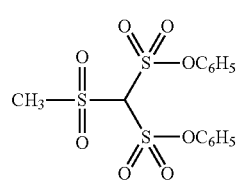

[formula 25]

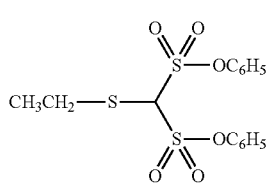

[formula 26]

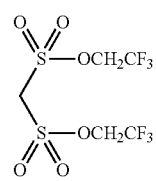

Compound No. 15

Compound No. 16

Compound No. 17

Compound No. 18

Compound No. 19

Compound No. 20

[formula 27]

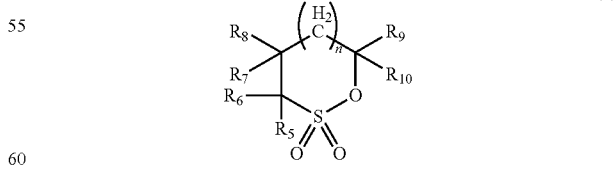

Although not particularly limited, the compound represented by the general formula (1) is preferably contained in an amount of 0.1 weight % to 5.0 weight % in the electrolyte solution. The effect may not be sufficiently exhibited below 0.1 weight % in the film formation through electrochemical reaction on the surface of the electrodes. If it exceeds 5.0 weight %, the compound is not only hard to be dissolved, but may increase the viscosity of the electrolyte solution. More preferably, the compound is added in a range of 0.5 weight % to 3.0 weight % in the present invention, which results in more sufficient film coating effect.

One compound represented by the general formula (1) may be used alone or two or more of them may be used in combination. When two or more of them are used in combination, although not particularly limited, it is effective from a viewpoint of the easiness of film formation on the electrodes that at least one compound having an active methylene group (that is, a compound in which $R_1$ and $R_4$ are hydrogen atoms) is contained. As a specific combination, they are compounds of the Compound No. 1 (compound which has an active methylene group) and Compound No. 5.

When two or more kinds of compounds of the general formula (1) are added to the electrolyte solution, although the ratio thereof in the electrolyte solution is not particularly limited, the two as a whole are preferably contained in an amount of 0.1 weight % to 5.0 weight % for the same reason as above. In addition, when two or more kinds of compounds of the general formula (1) are added, although the ratio of each compound to the total weight of the compounds of the general formula (1) is not particularly limited but it is preferable that the content of the least contained compound is 5 weight % and the content of the most contained compound is 95 weight %.

Furthermore, it is also effective to use an electrolyte solution which contains at least one of cyclic monosulfonates, cyclic sulfonates having two sulfonyl groups, alkane sulfonic anhydrides and sulfolene compounds in the electrolyte solution containing the compound of the general formula (1).

The cyclic monosulfonate include a compound represented by the following general formula (2):

[formula 28]

$$\text{(2)}$$

(structure shown)

wherein n is an integer of 0 to 2; $R_5$ to $R_{10}$ independently represent an atom or a group selected from a hydrogen atom, a substituted or unsubstituted alkyl group having 1 to 12 carbon atoms, a substituted or unsubstituted fluoroalkyl group having 1 to 6 carbon atoms, and a polyfluoroalkyl group having 1 to 6 carbon atoms.

From the viewpoint including stability of the compound, easiness of synthesis of the compound, solubility in a solvent and cost, n is preferably 0 or 1, and $R_5$ to $R_{10}$ preferably independently represent a atom or a group selected from a hydrogen atom, a substituted or unsubstituted alkyl group having 1 to 12 carbon atoms and a polyfluoroalkyl group having 1 to 5 carbon atoms, and more preferably independently represent a hydrogen atom or a polyfluoroalkyl group having 1 to 5 carbon atoms in the compound represented by the general formula (2). Still more preferably, all of $R_5$ to $R_{10}$ are hydrogen atoms, or one or two of $R_5$ to $R_{10}$ are polyfluoroalkyl groups having 1 to 5 carbon atoms and the others are hydrogen atoms. As a polyfluoroalkyl group having 1 to 5 carbon atoms mentioned above, trifluoromethyl group is preferable.

Specific examples thereof include 1,3-propane sultone (1,3-PS), α-trifluoromethyl-γ-sultone, β-trifluoromethyl-γ-sultone, γ-trifluoromethyl-γ-sultone, α-methyl-γ-sultone, α,β-di(trifluoromethyl)-γ-sultone, α,α-di(trifluoromethyl)-γ-sultone, α-undecafluoropentyl-γ-sultone, α-heptafluoropropyl-γ-sultone, 1,4-butane sultone (1,4-BS), etc.

It is considered that among these, 1,3-propane sultone (1,3-PS) forms a decomposition film on the anode of a secondary lithium-ion battery. LUMO of 1,3-PS is 0.07 eV, and is higher than that of Compound No. 1 of the present invention (−0.86 eV). For example, when Compound No. 1 of the present invention and 1,3-PS are added in the electrolyte solution and electrically charged, it is considered that the substance of Compound No. 1 forms a film on the anode first, and then 1,3-PS forms a film. Although a part of the anode surface mainly reacts and Compound No. 1 at the initial stage of charging, charging proceeds on the part which has not been reacted with the Compound No. 1 (the part which is possible to react with a solvent molecule) where reaction with 1,3-PS occurs, and consequently a composite film of Compound No. 1 and 1,3-PS is formed, the effects of suppressing further increase in the resistance and swell of battery, etc. can be expected.

When the compound of the general formula (2) is added in the electrolyte solution, the content thereof in the electrolyte solution is not particularly limited but it is preferably contained in an amount of 0.5 weight % to 10.0 weight % in the electrolyte solution. The effect may not be sufficiently exhibited below 0.5 weight % in the film formation through electrochemical reaction on the surface of the electrodes. If it exceeds 10.0 weight %, the viscosity of the electrolyte solution may increase. The ratio of the compound of the general formula (2) in the compounds of the general formula (1) and the general formula (2) is preferably 10 to 90 weight % based on the total weight of the compound of the general formula (1) and the compound of the general formula (2), respectively.

The cyclic sulfonate having two sulfonyl groups include a compound represented by the following general formula (3):

[formula 29]

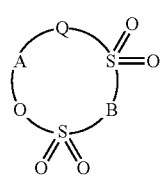

(3)

wherein Q represents an oxygen atom, an methylene group or a single bond, A represents a group selected from a substituted or unsubstituted alkylene group having 1 to 5 carbon atoms, a carbonyl group, a sulfinyl group, a polyfluoroalkylene group having 1 to 5 carbon atoms, a substituted or unsubstituted fluoroalkylene group having 1 to 5 carbon atoms, substituted or unsubstituted alkylene group having 1 to 5 carbon atoms in which at least one of C—C bonds is converted into a C—O—C bond, a polyfluoroalkylene group having 1 to 5 carbon atoms in which at least one of C—C bonds is converted into a C—O—C bond, and a substituted or unsubstituted fluoroalkylene group having 1 to 5 carbon atoms in which at least one of C—C bonds is converted into a C—O—C bond; and B represents a group selected from a substituted or unsubstituted alkylene group having 1 to 5 carbon atoms, a polyfluoroalkylene group having 1 to 5 carbon atoms, and a substituted or unsubstituted fluoroalkylene group having 1 to 5 carbon atoms.

From the viewpoint including stability of the compound, easiness of synthesis of the compound, solubility in a solvent and cost, A is preferably a group selected from a substituted or unsubstituted alkylene group having 1 to 5 carbon atoms, a polyfluoroalkylene group having 1 to 5 carbon atoms, a substituted or unsubstituted fluoroalkylene group having 1 to 5 carbon atoms, a substituted or unsubstituted alkylene group having 1 to 5 carbon atoms in which at least one of C—C bonds is converted into a C—O—C bond, a polyfluoroalkylene group having 1 to 5 carbon atoms in which at least one of C—C bonds is converted into a C—O—C bond, and a substituted or unsubstituted fluoroalkylene group having 1 to 5 carbon atoms in which at least one of C—C bonds is converted into a C—O—C bond. A group selected from a substituted or unsubstituted alkylene group having 1 to 5 carbon atoms, a polyfluoroalkylene group having 1 to 5 carbon atoms, and a substituted or unsubstituted fluoroalkylene group having 1 to 5 carbon atoms is more preferable, and a substituted or unsubstituted alkylene group having 1 to 5 carbon atoms is still more preferable, and a methylene group, an ethylene group or a 2,2-propanediyl group is particularly preferable in the compound represented by the general formula (3). The fluoroalkylene group having 1 to 5 carbon atoms mentioned above preferably includes a methylene group and a difluoromethylene group, and it is more preferably consisted of a methylene group and a difluoromethylene group.

For the same reason as above, B is preferably an alkylene group of having 1 to 5 carbon atoms, and more preferably methylene group, 1,1-ethanediyl group or 2,2-propanediyl group.

These cyclic sulfonates having two sulfonyl groups are disclosed in the specification of U.S. Pat. No. 4,950,768. Specific examples of the compound represented by the general formula (3) are shown below, but these are not restrictive examples.

[formula 30]

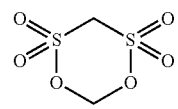

Compound No. 21

(methylenemethane disulfonic acid ester: MMDS)

[formula 31]
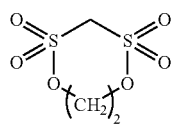
Compound No. 22
[formula 32]
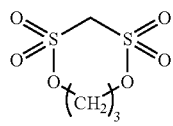
Compound No. 23
[formula 33]
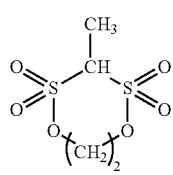
Compound No. 24
[formula 34]
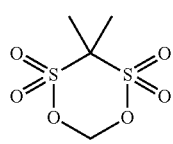
Compound No. 25
[formula 35]
Compound No. 26
[formula 36]
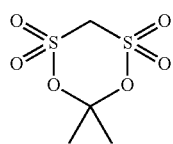
Compound No. 27
[formula 37]
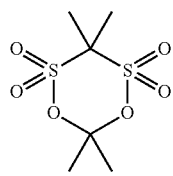
Compound No. 28
[formula 38]
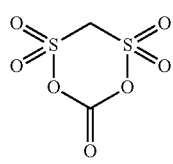
Compound No. 29
[formula 39]
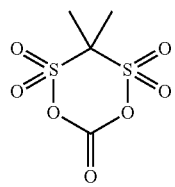
Compound No. 30
[formula 40]
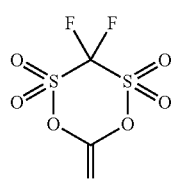
Compound No. 31
[formula 41]
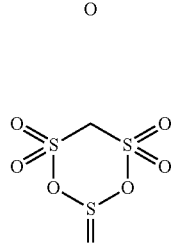
Compound No. 32
[formula 42]
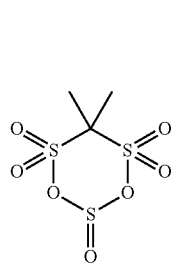
Compound No. 33
[formula 43]
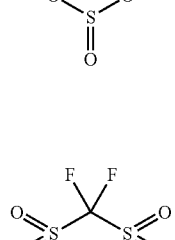
Compound No. 34
[formula 44]
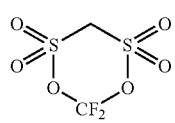
Compound No. 35
[formula 45]
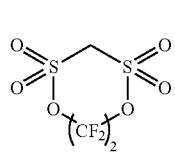
Compound No. 36

[formula 46]

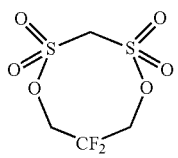

Compound No. 37

[formula 47]

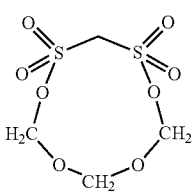

Compound No. 38

[formula 48]

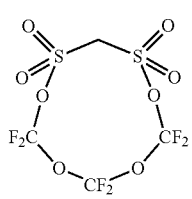

Compound No. 39

[formula 49]

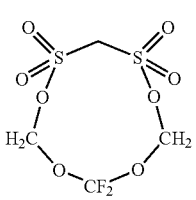

Compound No. 40

[formula 50]

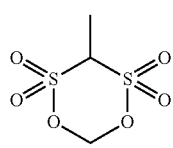

Compound No. 41

[formula 51]

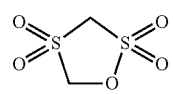

Compound No. 42

These compounds have LUMOs in the similar level to those of the compound of the general formula (1) of the present invention, and two or more sulfonyl groups, and if Compound No. 1 and Compound No. 21 (MMDS), for example, are added in the electrolyte solution, a composite film having a high ion conductivity can be easily formed at an initial stage of charging. MMDS is a cyclic compound and it is supposed that it readily form a film by reacting with the anode after the ring is opened.

If MMDS contributes to film formation quite selectively on the anode, the film formation probability of Compound No. 1 on the anode decreases and the reaction probability thereof on the cathode increases, and the film formation on the cathode is achieved. Consequently, suppression of the solvent decomposition on the cathode can be expected.

When the compound of the general formula (3) is added in the electrolyte solution, the content thereof in the electrolyte solution is not particularly limited but it is preferably contained in an amount of 0.5 weight % to 10.0 weight % in the electrolyte solution. The effect may not be sufficiently exhibited below 0.5 weight % in the film formation through electrochemical reaction on the surface of the electrodes. If it exceeds 10.0 weight %, the viscosity of the electrolyte solution may increase. The ratio of the compound of the general formula (3) in the compounds of the general formula (1) and the general formula (3) is preferably 10 to 90 weight % based on the total weight of the compound of the general formula (1) and the general formula (3). When the compound of the general formula (2) is used in addition to them, it is preferably 10 to 90 weight % based on the total weight of the compound of the general formula (1), general formula (2) and general formula (3).

In the present invention, in some cases at least one of vinylene carbonate (VC) and the derivatives thereof can be added in the electrolyte solution. An improvement of the cycle characteristic can be further achieved by adding at least one of VC and the derivatives thereof. LUMO of VC is 0.09 eV and it is supposed that it is less susceptible to reduction reaction and exists in the electrolyte solution over a long period of time without being consumed in the reduction reaction at an initial stage of charge/discharge compared with the compound of the general formula (1). Therefore, it can contribute to the improvement in the cycle characteristics by being gradually consumed at the time of charge/discharge cycles. When at least one of the vinylene carbonate (VC) and the derivatives thereof is used as an additive to the electrolyte solution, the effect thereof can be obtained by the addition of 0.05 weight % to 3.0 weight % to the electrolyte solution.

When the compound of the general formula (1) and VC, the compound of the general formula (1) and the other additive and VC are further added in the electrolyte solution, the ratio of VC in the whole electrolyte solution is not particularly limited but it is preferably 0.5 weight % to 10.0 weight %. The effect may not be sufficiently exhibited below 0.5 weight % in the film formation through electrochemical reaction on the surface of the electrodes. If it exceeds 10.0 weight %, the viscosity of the electrolyte solution may increase.

The electrolyte solution of the present invention can be provided by adding and dissolving beforehand the compound represented by the general formula (1) in the electrolyte solution. The desired electrolyte solution can be obtained by adding suitably the other additives (cyclic monosulfonate, cyclic sulfonate having two sulfonyl groups, sulfolane, alkane sulfonic anhydride, sulfolene compound, or vinylene carbonate compound) to this electrolyte solution.

The shape of the secondary battery of the present invention is not particularly limited, and includes a cylinder type, a rectangular type, a coin type, a laminate type, for example. Among these, the laminate type has a shape sealed in a jacket which consists of a flexible film comprising of a laminate of a synthetic resin and a metal foil, and is readily affected by the increase of inner pressure as compared with those enclosed in a jacket which consists of a battery can of a cylinder type, a rectangular shape and a coin type, therefore control of chemical reaction on the interface of the electrodes and the electrolyte solution is more important. If it is a secondary battery containing a linear disulfone compound represented by the general formula (1) of the present invention, suppression of the increase of resistance, and battery swelling (due to the generation of gas and increase of inner pressure) is possible even in a laminate type battery. Therefore, it becomes possible to secure safety and reliability over a long period of time even in large-sized secondary lithium ion batteries such as those used in an automobile.

The lithium secondary battery of the present invention can be obtained by laminating an anode 13 and a cathode 12 with a separator 16 positioned therebetween or rolling such a laminate and placing it into a jacket in a dry air or inactive gas atmosphere, and after impregnating it with an electrolyte solution containing the compound represented by a general formula (1), sealing the battery jacket. It is possible to obtain the effect of the present invention by forming the films on the electrodes by charging a battery before or after sealing.

In addition, the linear disulfonate represented by the general formula (1) of the present invention can be used as an additive of electrolyte solution not only for a lithium secondary battery but also for the other electrochemical devices. Examples of the other electrochemical devices include an organic radical battery, a capacitor and a dye sensitized wet-type solar cell.

EXAMPLES (Fabrication of Battery)

Cathode active material given in Tables 1 to 5 and a conductivity imparting agent were subjected to dry-type mixing, and uniformly dispersed in N-methyl-2-pyrrolidone (NMP) in which PVDF serving as a binder has been dissolved to prepare a slurry. Carbon black was used as a conductivity imparting agent. The slurry was applied on an aluminum metal foil (20 pm in the case of a cylinder type and 25 pm in the case of a laminated type) serving as cathode current collector and NMP was evaporated to form a cathode sheet. The solid content ratio in the cathode was cathode active material: conductivity imparting agent:PVDF=80:10:10 (weight %).

On the other hand, when an anode active material consists of a carbon material, carbon and PVDF are mixed so that carbon:PVDF=90:10 (weight %), dispersed in NMP and applied on a copper foil (10 pm in the case of a coin type and cylinder type and 20 pm in the case of a laminated type) serving as anode current collector 14.

The electrolyte solutions 15 comprising the solvents given in Tables 1 to 5, 1 mol/L of $LiPF_6$ as an electrolyte and additives given in Tables 1 to 5 were used.

After that, cylinder type secondary battery (Examples 1 to 23, Comparative Examples 1 and 2) and the aluminum laminate film type secondary battery (Examples 24 to 53, Comparative Examples 3 to 11) were fabricated by laminating an anode and a cathode with a separator 16 which consists of polyethylene therebetween. In the case of an aluminum laminate film type secondary battery, the used laminate film had a structure in which polypropylene resin (melt sealing layer, thickness of 70 μm), polyethylene terephthalate (20 μm), aluminum (50 μm), and polyethylene terephthalate (20 μm) were laminated in this order. These were cut into two sheets of a predetermined size, and recessed parts were formed in some parts thereof which had bottom and side portions which were suited for the size of the laminate electrode. These were positioned face to face to enclose the laminate electrode and the circumference thereof was heat-sealed to form a film jacketed battery. Before the last one side was heat-sealed, the laminate electrode was impregnated with an electrolyte solution.

(Charge/Discharge Cycle Test)

The charge rate and discharge rate were adjusted to 1 C respectively, and the charge termination voltage to 4.2 V and the discharge termination voltage to 2.5 V. The capacity retention ratio is a value obtained by dividing a discharge capacity (mAh) after 500 cycles by a discharge capacity (mAh) of the tenth cycle.

(Test of Characteristics after Storage)

The characteristics after storage was estimated by the ratio of increase in the resistance after the stored for 60 days at 50% (45° C.) discharge depth (the ratio of the resistance after storage assuming that the initial resistance (at the time of beginning storage) was 1; the charge/discharge conditions were the same as in the charge/discharge cycle test).

TABLE 1

| | Cathode Active Material | Anode Active Material | Type and Content of the Additive in the Electrolyte solution (weight %) | Solvent (Volume Ratio) | Shape of the Cell |
| --- | --- | --- | --- | --- | --- |
| Example 1 | $LiMn_2O_4$ | Amorphous Carbon | No. 1(0.5) | PC/EC/DEC (20/20/60) | Cylinder type |
| Example 2 | $LiMn_2O_4$ | Amorphous Carbon | No. 2(0.5) | PC/EC/DEC (20/20/60) | Cylinder type |
| Example 3 | $LiMn_2O_4$ | Amorphous Carbon | No. 3(0.5) | PC/EC/DEC (20/20/60) | Cylinder type |
| Example 4 | $LiMn_2O_4$ | Amorphous Carbon | No. 4(0.5) | PC/EC/DEC (20/20/60) | Cylinder type |
| Example 5 | $LiMn_2O_4$ | Amorphous Carbon | No. 6(0.5) | PC/EC/DEC (20/20/60) | Cylinder type |
| Example 6 | $LiMn_2O_4$ | Amorphous Carbon | No. 9(0.5) | PC/EC/DEC (20/20/60) | Cylinder type |
| Example 7 | $LiMn_2O_4$ | Amorphous Carbon | No. 10(0.5) | PC/EC/DEC (20/20/60) | Cylinder type |
| Example 8 | $LiMn_2O_4$ | Amorphous Carbon | No. 15(0.5) | PC/EC/DEC (20/20/60) | Cylinder type |
| Example 9 | $LiMn_2O_4$ | Amorphous Carbon | No. 19(0.5) | PC/EC/DEC (20/20/60) | Cylinder type |
| Example 10 | $LiMn_2O_4$ | Amorphous Carbon | No. 16(0.5) | PC/EC/DEC (20/20/60) | Cylinder type |
| Comparative Example 1 | $LiMn_2O_4$ | Amorphous Carbon | None | PC/EC/DEC (20/20/60) | Cylinder type |
| Comparative Example 2 | $LiMn_2O_4$ | Amorphous Carbon | 1% 1,3-PS | PC/EC/DEC (20/20/60) | Cylinder type |

TABLE 2

| | Cathode Active Material | Anode Active Material | Type and Content of the Additive in the Electrolyte solution (weight %) | Solvent (Volume Ratio) | Shape of the Cell |
|---|---|---|---|---|---|
| Example 11 | $LiMn_2O_4$ | Amorphous Carbon | No. 1(0.01) | PC/EC/DEC (20/20/60) | Cylinder type |
| Example 12 | $LiMn_2O_4$ | Amorphous Carbon | No. 1(0.05) | PC/EC/DEC (20/20/60) | Cylinder type |
| Example 13 | $LiMn_2O_4$ | Amorphous Carbon | No. 1(0.075) | PC/EC/DEC (20/20/60) | Cylinder type |
| Example 14 | $LiMn_2O_4$ | Amorphous Carbon | No. 1(0.1) | PC/EC/DEC (20/20/60) | Cylinder type |
| Example 15 | $LiMn_2O_4$ | Amorphous Carbon | No. 1(0.75) | PC/EC/DEC (20/20/60) | Cylinder type |
| Example 16 | $LiMn_2O_4$ | Amorphous Carbon | No. 1(1.0) | PC/EC/DEC (20/20/60) | Cylinder type |
| Example 17 | $LiMn_2O_4$ | Amorphous Carbon | No. 1(2.0) | PC/EC/DEC (20/20/60) | Cylinder type |
| Example 18 | $LiMn_2O_4$ | Amorphous Carbon | No. 1(3.0) | PC/EC/DEC (20/20/60) | Cylinder type |
| Example 19 | $LiMn_2O_4$ | Amorphous Carbon | No. 1(5.0) | PC/EC/DEC (20/20/60) | Cylinder type |
| Example 20 | $LiMn_2O_4$ | Amorphous Carbon | No. 1(6.0) | PC/EC/DEC (20/20/60) | Cylinder type |
| Example 21 | $LiMn_2O_4$ | Amorphous Carbon | No. 1(7.5) | PC/EC/DEC (20/20/60) | Cylinder type |
| Example 22 | $LiMn_2O_4$ | Amorphous Carbon | No. 1(10.0) | PC/EC/DEC (20/20/60) | Cylinder type |
| Example 23 | $LiMn_2O_4$ | Amorphous Carbon | No. 1(12.5) | PC/EC/DEC (20/20/60) | Cylinder type |

TABLE 3

| | Cathode Active Material | Anode Active Material | Type and Content of the Additive in the Electrolyte solution (weight %) | Solvent (Volume Ratio) | Shape of the Cell |
|---|---|---|---|---|---|
| Example 24 | $LiMn_2O_4$ | Graphite | No. 1(1.5) | PC/EC/DEC (20/20/60) | Laminate type |
| Example 25 | $LiMn_2O_4$ | Graphite | No. 1(1.5) + 0.5% 1,3-PS | PC/EC/DEC (20/20/60) | Laminate type |
| Example 26 | $LiMn_2O_4$ | Graphite | No. 1(1.5) + 0.5% 1,4-BS | PC/EC/DEC (20/20/60) | Laminate type |
| Example 27 | $LiMn_2O_4$ | Graphite | No. 1(1.5) + 0.5% 1,3-PS + 0.5% VC | PC/EC/DEC (20/20/60) | Laminate type |
| Example 28 | $LiMn_2O_4$ | Graphite | No. 1(1.5) + 0.5% MMDS | PC/EC/DEC (20/20/60) | Laminate type |
| Example 29 | $LiMn_2O_4$ | Graphite | No. 1(1.5) + 0.5% MMDS + 0.5% VC | PC/EC/DEC (20/20/60) | Laminate type |
| Comparative Example 3 | $LiMn_2O_4$ | Graphite | None | PC/EC/DEC (20/20/60) | Laminate type |
| Comparative Example 4 | $LiMn_2O_4$ | Graphite | +0.5% 1,3-PS + 1.5% VC | PC/EC/DEC (20/20/60) | Laminate type |

TABLE 4

| | Cathode Active Material | Anode Active Material | Type and Content of the Additive in the Electrolyte solution (weight %) | Solvent (Volume Ratio) | Shape of the Cell |
|---|---|---|---|---|---|
| Example 30 | $LiMnO_2$ | Amorphous Carbon | No. 1(0.5) | PC/EC/DEC (20/20/60) | Laminate type |
| Example 31 | $LiMnO_2$ | Amorphous Carbon | No. 2(0.5) | PC/EC/DEC (20/20/60) | Laminate type |
| Example 32 | $LiMnO_2$ | Amorphous Carbon | No. 3(0.5) | PC/EC/DEC (20/20/60) | Laminate type |
| Example 33 | $LiMnO_2$ | Amorphous Carbon | No. 4(0.5) | PC/EC/DEC (20/20/60) | Laminate type |
| Example 34 | $LiMnO_2$ | Amorphous Carbon | No. 6(0.5) | PC/EC/DEC (20/20/60) | Laminate type |

TABLE 4-continued

| | Cathode Active Material | Anode Active Material | Type and Content of the Additive in the Electrolyte solution (weight %) | Solvent (Volume Ratio) | Shape of the Cell |
|---|---|---|---|---|---|
| Example 35 | $LiMnO_2$ | Amorphous Carbon | No. 9(0.5) | PC/EC/DEC (20/20/60) | Laminate type |
| Example 36 | $LiMnO_2$ | Amorphous Carbon | No. 10(0.5) | PC/EC/DEC (20/20/60) | Laminate type |
| Example 37 | $LiMnO_2$ | Amorphous Carbon | No. 15(0.5) | PC/EC/DEC (20/20/60) | Laminate type |
| Example 38 | $LiMnO_2$ | Amorphous Carbon | No. 19(0.5) | PC/EC/DEC (20/20/60) | Laminate type |
| Example 39 | $LiMnO_2$ | Amorphous Carbon | No. 16(0.5) | PC/EC/DEC (20/20/60) | Laminate type |
| Example 40 | $LiMnO_2$ | Amorphous Carbon | No. 1(0.05) | PC/EC/DEC (20/20/60) | Laminate type |
| Example 41 | $LiMnO_2$ | Amorphous Carbon | No. 1(0.1) | PC/EC/DEC (20/20/60) | Laminate type |
| Example 42 | $LiMnO_2$ | Amorphous Carbon | No. 1(1.0) | PC/EC/DEC (20/20/60) | Laminate type |
| Example 43 | $LiMnO_2$ | Amorphous Carbon | No. 1(3.0) | PC/EC/DEC (20/20/60) | Laminate type |
| Example 44 | $LiMnO_2$ | Amorphous Carbon | No. 1(5.0) | PC/EC/DEC (20/20/60) | Laminate type |
| Example 45 | $LiMnO_2$ | Amorphous Carbon | No. 1(6.0) | PC/EC/DEC (20/20/60) | Laminate type |
| Example 46 | $LiMnO_2$ | Amorphous Carbon | No. 1(7.5) | PC/EC/DEC (20/20/60) | Laminate type |
| Example 47 | $LiMnO_2$ | Amorphous Carbon | No. 1(10.0) | PC/EC/DEC (20/20/60) | Laminate type |

TABLE 5

| | Cathode Active Material | Anode Active Material | Type and Content of the Additive in the Electrolyte solution (weight %) | Solvent (Volume Ratio) | Shape of the Cell |
|---|---|---|---|---|---|
| Example 48 | $LiMnO_2$ | Amorphous Carbon | No. 1(0.5) + 0.5% 1,3-PS | PC/EC/DEC (20/20/60) | Laminate type |
| Example 49 | $LiMnO_2$ | Amorphous Carbon | No. 1(0.5) + 0.5% 1,4-BS | PC/EC/DEC (20/20/60) | Laminate type |
| Example 50 | $LiMnO_2$ | Amorphous Carbon | No. 1(0.5) + 0.5% MMDS | PC/EC/DEC (20/20/60) | Laminate type |
| Example 51 | $LiMnO_2$ | Amorphous Carbon | No. 1(0.5) + 0.5% MMDS + 0.5% VC | PC/EC/DEC (20/20/60) | Laminate type |
| Example 52 | $LiMnO_2$ | Amorphous Carbon | No. 1(0.5) + 0.5% 1,3-PS + 0.5% VC | PC/EC/DEC (20/20/60) | Laminate type |
| Example 53 | $LiMnO_2$ | Amorphous Carbon | No. 1(0.5) + 0.5% 1,4-BS + 0.5% VC | PC/EC/DEC (20/20/60) | Laminate type |
| Comparative Example 5 | $LiMnO_2$ | Amorphous Carbon | None | PC/EC/DEC (20/20/60) | Laminate type |
| Comparative Example 6 | $LiMnO_2$ | Amorphous Carbon | 0.5% 1,3-PS | PC/EC/DEC (20/20/60) | Laminate type |
| Comparative Example 7 | $LiMnO_2$ | Amorphous Carbon | 0.5% 1,4-BS | PC/EC/DEC (20/20/60) | Laminate type |
| Comparative Example 8 | $LiMnO_2$ | Amorphous Carbon | 0.5% MMDS | PC/EC/DEC (20/20/60) | Laminate type |
| Comparative Example 9 | $LiMnO_2$ | Amorphous Carbon | 0.5% 1,3-PS + 0.5% VC | PC/EC/DEC (20/20/60) | Laminate type |
| Comparative Example 10 | $LiMnO_2$ | Amorphous Carbon | 0.5% 1,4-BS + 0.5% VC | PC/EC/DEC (20/20/60) | Laminate type |
| Comparative Example 11 | $LiMnO_2$ | Amorphous Carbon | 0.5% MMDS + 0.5% VC | PC/EC/DEC (20/20/60) | Laminate type |

"No." in the "Type and Content of the Additive in the Electrolyte solution" column in Tables 1 to 5 refers to Compound No.

In addition, the results obtained by the cycle test and the test after storage are shown in the following Tables 6 to Table 10. The resistance increase ratio in the characteristics after storage is a relative value assuming that the initial value is 1.

TABLE 6

| | Capacity retention ratio (%) at 500 cycle | Characteristics after Storage (Resistance Increase Ratio) |
|---|---|---|
| Example 1 | 90.1 | 1.055 |
| Example 2 | 89.8 | 1.082 |
| Example 3 | 90.4 | 1.078 |

TABLE 6-continued

| | Capacity retention ratio (%) at 500 cycle | Characteristics after Storage (Resistance Increase Ratio) |
|---|---|---|
| Example 4 | 90.5 | 1.077 |
| Example 5 | 90.1 | 1.061 |
| Example 6 | 89.3 | 1.089 |
| Example 7 | 88.4 | 1.095 |
| Example 8 | 86.6 | 1.068 |
| Example 9 | 86.4 | 1.066 |
| Example 10 | 85.9 | 1.078 |
| Comparative Example 1 | 76.4 | 1.512 |
| Comparative Example 2 | 80.9 | 1.384 |

TABLE 7

| | Capacity retention ratio (%) at 500 cycle | Characteristics after Storage (Resistance Increase Ratio) |
|---|---|---|
| Example 11 | 80.1 | 1.213 |
| Example 12 | 81.5 | 1.209 |
| Example 13 | 82.6 | 1.193 |
| Example 14 | 87.8 | 1.098 |
| Example 15 | 90.8 | 1.069 |
| Example 16 | 90.7 | 1.055 |
| Example 17 | 90.6 | 1.089 |
| Example 18 | 90.3 | 1.078 |
| Example 19 | 90.0 | 1.081 |
| Example 20 | 85.5 | 1.123 |
| Example 21 | 82.6 | 1.135 |
| Example 22 | 81.9 | 1.165 |
| Example 23 | 81.5 | 1.198 |

TABLE 8

| | Capacity retention ratio (%) at 500 cycle | Characteristics after Storage (Resistance Increase Ratio) | | |
|---|---|---|---|---|
| | | Resistance Increase Ratio | Capacity Recovery Ratio(%) | Change in Cell Volume ×$10^{-6}$($m^3$) |
| Example 24 | 89.2 | 1.089 | 90.6 | 0.22 |
| Example 25 | 91.2 | 1.068 | 89.1 | 0.12 |
| Example 26 | 91.0 | 1.082 | 88.7 | 0.14 |
| Example 27 | 92.9 | 1.053 | 88.4 | 0.18 |
| Example 28 | 91.1 | 1.102 | 91.1 | 0.16 |
| Example 29 | 92.8 | 1.068 | 90.1 | 0.20 |
| Comparative Example 3 | 77.4 | 1.526 | 79.4 | 0.63 |
| Comparative Example 4 | 81.3 | 1.298 | 82.1 | 0.34 |

TABLE 9

| | Capacity retention ratio (%) at 500 cycle | Characteristics after Storage (Resistance Increase Ratio) |
|---|---|---|
| Example 30 | 87.5 | 1.109 |
| Example 31 | 86.2 | 1.125 |
| Example 32 | 88.1 | 1.106 |
| Example 33 | 87.6 | 1.138 |
| Example 34 | 87.9 | 1.126 |
| Example 35 | 86.5 | 1.165 |
| Example 36 | 86.0 | 1.155 |
| Example 37 | 85.2 | 1.135 |
| Example 38 | 85.1 | 1.144 |
| Example 39 | 85.6 | 1.138 |
| Example 40 | 80.3 | 1.256 |
| Example 41 | 84.7 | 1.187 |
| Example 42 | 87.1 | 1.138 |
| Example 43 | 86.8 | 1.135 |
| Example 44 | 87.5 | 1.142 |
| Example 45 | 82.3 | 1.186 |
| Example 46 | 81.6 | 1.203 |
| Example 47 | 80.9 | 1.239 |

TABLE 10

| | Capacity retention ratio (%) at 500 cycle | Characteristics after Storage (Resistance Increase Ratio) |
|---|---|---|
| Example 48 | 89.2 | 1.083 |
| Example 49 | 88.9 | 1.088 |
| Example 50 | 89.1 | 1.091 |
| Example 51 | 91.1 | 1.056 |
| Example 52 | 90.9 | 1.053 |
| Example 53 | 90.7 | 1.059 |
| Comparative Example 5 | 76.3 | 1.516 |
| Comparative Example 6 | 80.6 | 1.346 |
| Comparative Example 7 | 80.2 | 1.389 |
| Comparative Example 8 | 79.5 | 1.378 |
| Comparative Example 9 | 81.9 | 1.298 |
| Comparative Example 10 | 81.3 | 1.268 |
| Comparative Example 11 | 81.6 | 1.274 |

(Effect by Addition of the Compound of the General Formula (1))

The capacity retention ratios in Examples 1 to 10 and Examples 30 to 39 are respectively compared with those in Comparative Examples 1 and 2, and 5 to 11, a significant improvement in the cycle characteristics and extensive control of the characteristics after storage were confirmed in Examples 1 to 10 and Examples 30 to 39. In addition, as for the batteries shown in Examples 1 to 10 and Examples 30 to 39, the anode and cathode surfaces after cycle test were investigated with X-ray photoelectron spectroscopy (XPS) and energy dispersive X-ray analysis (EDX), which revealed the existence of LiF, $LiCO_3$, etc. Furthermore, as a result of performing peak division of the sulfur spectrum by XPS analysis, it was confirmed that the substance having a peak near 164 eV existed in both the cathode and anode. There was no substance having a peak near 164 eV in each of the cathode and anode in Comparative Example 1 and in the cathode of the system using an additive in Comparative Example 2, and it is supposed that a film peculiar to the linear disulfone acid of the present invention was formed.

(Influence of the Concentration of the Compound of the General Formula (1) in Electrolyte Solution)

The concentration of Compound No. 1 occupied in the electrolyte solution was varied in Examples 11 to 23 and Examples 40 to 47, and the fabricated secondary batteries were evaluated. The capacity retention ratio after 500 cycles decreased when the concentration was below 0.1 weight % and exceeded 5.0 weight %. Moreover, it turned out that the resistance increase ratio after 60 days storage increased when the concentration was below 0.1 weight % and exceeded 5.0 weight %. From this result, it has been confirmed that the concentration of the compound of the general formula (1) in the 865 electrolyte solution is preferably 0.1 weight % to 5.0 weight %, and the particularly preferable concentration range is 0.5 weight % to 3.0 weight %.

(Evaluation of Characteristics of Laminate Film Type Battery)

Laminated type batteries of Examples 24 to 29 and Comparative Examples 3 and 4 were used and they were charged with a constant current of 2A and a constant voltage for 5 hours to termination voltage 4.3 V at room temperature (25° C.), and then discharged with a constant current of 2 A to termination voltage 2.5V, and the generated gas was removed and the volume of the battery at this time was measured. After the gas was removed and the batteries were left standing for one week, they were charged and discharged one time again respectively at room temperature. The charge current and discharge current at this time were fixed (2 A), and the discharge capacity at this time was regarded as the initial capacity. The cutoff potential on the side of discharge was adjusted to 2.5 V and the cutoff potential on the side of charge was adjusted to 4.3 V. Then, after charged for 2.5 hours to 4.2 V with a constant current of 2 A and a constant voltage, the batteries were discharged to 50% of discharge depth and left standing at 55° C. for 84 days. After the batteries were left standing, discharging operations were again performed with a constant current at room temperature, and then charging and discharging were similarly repeated with a constant current one more time, and the discharge capacity at this time was regarded as recovery capacity. Here, the ratio of capacity recovery was determined as (recovery capacity)/(initial capacity). The volumes of batteries were measured simultaneously and the difference with the volume immediately after the gas was removed was regarded as the amount of cell volume change.

In addition, as for the laminated type batteries of Examples 24 to 47 and Comparative Examples 3 to 11, the resistance increase rate and the capacity retention ratio after 500 cycles were measured.

(Effect of the Addition of the Compound of the General Formula (1) in a Laminate Film Type Battery)

The ratio of capacity recovery after the storage and the capacity retention ratio after 500 cycles in Example 24 and the capacity retention ratio after the 500 cycles in Examples 30 to 47 were greatly improved as compared with those in Comparative Example 3 and Comparative Example 5 in which the compound of the general formula (1) was not added. In addition, the resistance increase rate after storage was greatly suppressed as compared with those in Comparative Example 3 and Comparative Example 5 in which the compound was not added. These results are considered to be resulted from the fact that a film having higher ion conductivity and high stability after storage as compared with additive-free systems or conventional additive systems was formed by the addition of the compound represented by the general formula (1) of the present invention in the electrolyte solution. Furthermore, as for the amount of volume change of the laminate jacket cell after storage, the amount of volume change of the cell of Example 24 is smaller than that in Comparative Example 3 and Comparative Example 4. This is considered to be attributable to the fact that decomposition film of compound (1) was formed on the electrode and suppressed the generation of gas resulted from decomposition of the electrolyte solution.

(Effect of the Addition of the Cyclic Monosulfonate in a Laminate Film Type Battery)

The amount of cell volume change in Example 25 and Example 26 is smaller than that in Comparative Example 3, Comparative Example 4 and Example 24. This is considered to be attributable to the composite effect of the compound (1) and 1,3-PS or 1,4-BS, which formed a film on the anode and greatly suppressed the generation of gas resulted from decomposition of the electrolyte solution.

(Effect of the Addition of the Cyclic Sulfonate Having Two Sulfonyl Groups in a Laminate Film Type Battery)

The ratio of capacity recovery and the capacity retention ratio after 500 cycles in Example 28 were further improved as compared with Example 24. The capacity retention ratio after the 500 cycles in Example 50 was also further improved as compared with Example 30. These results are considered to be resulted from the fact that a film having higher ion conductivity and high stability after storage as compared with additive-free systems or conventional additive systems was formed by the addition of the compound represented by the general formula (1) of the present invention and the cyclic sulfonate having two sulfonyl groups in the electrolyte solution. The amount of volume change of the cell in Example 28 is smaller than that in Comparative Example 3, Comparative Example 4, and Example 24. This is considered to be attributable to the composite effect of the compound (1) and MMDS, which formed a film on the anode and greatly suppressed the generation of gas resulted from decomposition of the electrolyte solution.

(Effect of the Addition of VC in a Laminate Film Type Battery)

The cycle characteristics of the cell in Examples 27, 52 and 53 were further improved as compared with Examples 25, 48 and 49. These results are considered to be resulted from the fact that a film having higher ion conductivity and high stability after storage or charge/discharge cycles as compared with additive-free systems or conventional additive systems was formed by the addition of the compound represented by the general formula (1) of the present invention and the cyclic monosulfonate and vinylene carbonate in the electrolyte solution. In addition, the cycle characteristics of the cell in Examples 29 and 51 were improved as compared with Examples 28 and 50. These results are considered to be resulted from the fact that a film having higher ion conductivity and high stability after storage or charge/discharge cycles as compared with additive-free systems or conventional additive systems was formed by the addition of the compound represented by the general formula (1) of the present invention and the cyclic sulfonate having two sulfonyl groups and vinylene carbonate in the electrolyte solution.

The invention claimed is:

1. A secondary battery having a cathode, an anode and an electrolyte solution for secondary battery characterized in that the electrolyte solution for secondary battery comprises at least an aprotic solvent having an electrolyte dissolved therein and a compound represented by the following general formula (1):

[formula 1]

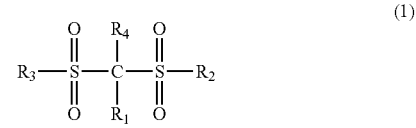

(1)

wherein $R_1$ and $R_4$ independently represent an atom or a group selected from a hydrogen atom, a substituted or unsubstituted alkyl group having 1 to 5 carbon atoms, a substituted or unsubstituted alkoxy group having 1 to 5 carbon atoms, a substituted or unsubstituted fluoroalkyl group having 1 to 5 carbon atoms, a polyfluoroalkyl group having 1 to 5 carbon atoms, —$SO_2X_1$, wherein $X_1$ is a substituted or unsubstituted alkyl group having 1 to 5 carbon atoms, —$SY_1$, wherein $Y_1$ is a substituted or unsubstituted alkyl group having 1 to 5 carbon atoms, —COZ, wherein Z is a hydrogen atom or a substituted or unsubstituted alkyl group having 1 to 5 carbon atoms, and a halogen atom; and $R_2$ and $R_3$ independently represent an atom or a group selected from a substituted or unsubstituted alkyl group having 1 and 3 to 5 carbon atoms, a substituted or unsubstituted alkoxy group having 1 to 5 carbon atoms, a substituted or unsubstituted phenoxy group, a substituted or unsubstituted fluoroalkyl group having 1 to 5 carbon atoms, a polyfluoroalkyl group having 1 to 5 carbon atoms, a substituted or unsubstituted fluoroalkoxy group having 1 to 5 carbon atoms, a polyfluoroalkoxy group having 1 to 5 carbon atoms, a hydroxyl group, a halogen atom, —$NX_2X_3$, wherein $X_2$ and $X_3$ independently represent a hydrogen atom or a substituted or unsubstituted alkyl group having 1 to 5 carbon atoms, and —$NY_2CONY_3Y_4$, wherein $Y_2$ to $Y_4$ independently represent a hydrogen atom or a substituted or unsubstituted alkyl group having 1 to 5 carbon atoms.

2. The secondary battery according to claim 1, wherein the anode comprises lithium metal or carbon as an anode active material.

3. The secondary battery according to claim 2, wherein the anode comprises graphite or amorphous carbon as the carbon.

4. The secondary battery according to claim 1, wherein the secondary battery is covered with a laminate jacket.

5. The secondary battery according to claim 2, wherein the secondary battery is covered with a laminate jacket.

6. The secondary battery according to claim 3, wherein the secondary battery is covered with a laminate jacket.

* * * * *